United States Patent [19]
Oppelt et al.

[11] Patent Number: 5,370,120
[45] Date of Patent: Dec. 6, 1994

[54] ULTRASOUND IMAGING APPARATUS

[75] Inventors: Sylvester Oppelt, Memmelsdorf; Arnim Rohwedder, Fuerth, both of Germany

[73] Assignee: Siemens Aktiengesellschaft, Munich, Germany

[21] Appl. No.: 150,989

[22] Filed: Nov. 12, 1993

[30] Foreign Application Priority Data

Dec. 8, 1992 [DE] Germany .............. 4241339
Sep. 13, 1993 [DE] Germany .............. 4331020

[51] Int. Cl.⁵ ............................................ A61B 8/00
[52] U.S. Cl. ........................... 128/660.03; 128/916; 128/663.01
[58] Field of Search ............ 128/660.03, 660.01, 128/660.07, 661.01, 660.09, 916, 663.01; 310/326, 334

[56] References Cited

U.S. PATENT DOCUMENTS

| | | | |
|---|---|---|---|
| 4,526,168 | 7/1985 | Hassler et al. | 128/24 EL |
| 4,570,488 | 2/1986 | Miwa et al. | 128/916 |
| 4,672,591 | 6/1987 | Breimesser et al. | 310/326 |
| 4,697,588 | 10/1987 | Reichenberger | 128/24 EL |
| 4,945,915 | 8/1990 | Nagasaki | 128/661.01 |
| 5,005,579 | 4/1991 | Wurster et al. | 128/660.03 |
| 5,027,820 | 7/1991 | Pesque | 128/916 |
| 5,065,763 | 11/1991 | Green et al. | 128/660.07 |
| 5,072,722 | 12/1991 | Granz | 128/660.03 |

OTHER PUBLICATIONS

"A Two Dimensional PVDF Transducer Matrix as a Receiver in an Ultrasonic Transmission Camera," Granz et al., Acoust. Imag., vol. 15, (1987) pp. 213–225.
"A New, High-Performance Ultrasonic Camera," Green et al., Acoustical Holography, vol. 5 (1973), pp. 493–503.

Primary Examiner—George Manuel
Attorney, Agent, or Firm—Hill, Steadman & Simpson

[57] ABSTRACT

An ultrasound imaging apparatus employs an ultrasound sensor arrangement formed by an at least two-dimensional sensor matrix and an imaging lens to generate signals which are used to calculate a true-to-scale, real-time, three-dimensional image of a subject according to the pulse-echo principle. A therapy apparatus using such an ultrasound imaging apparatus as its locating system is also disclosed.

37 Claims, 5 Drawing Sheets

ULTRASOUND IMAGING APPARATUS

BACKGROUND OF THE INVENTION

1. Field of the Invention

The present invention is directed to an ultrasound imaging apparatus for producing an ultrasound image of a subject, and is also directed to a therapy system for treating a subject (region) located in the body of a patient with focused acoustic waves, the therapy system containing an ultrasound imaging apparatus as a locating system for the region to be treated.

2. Description of the Prior Art

Conventional ultrasound imaging systems usually produce a two-dimensional image of a subject. Leaving systems referred to as ultrasound cameras U.S. Pat. No. 5,072,722 out of consideration, the image that is produced in known systems is usually a tomogram of the subject such as, for example, a B-mode ultrasound image U.S. Pat. No. 4,526,168. Three-dimensional ultrasound images can usually be produced only with great complexity, for example by chronologically successive production of a plurality of ultrasound tomograms covering different regions of the subject from which the data for producing a three-dimensional ultrasound image are then extracted U.S. Pat. No. 5,005,579. Such a procedure is complicated and time-consuming in comparison to the standard ultrasound tomogram imaging apparatus that supplies real-time images. Therapy systems for treating subjects (regions) located in the body of a patient with focused acoustic waves therefore almost exclusively contain ultrasound imaging systems, which only supply tomograms, as the locating system.

For a more efficient treatment and a treatment that would be gentler on the patient, however, there is a need to have additional image information with respect to the subject to be treated available, which would allow a better alignment of the therapy means and the body of the patient relative to one another.

SUMMARY OF THE INVENTION

An object of the present invention is to provide an ultrasound imaging system that allows spatial ultrasound images of a subject to be prepared in a simple, time-saving, and thus economic way.

A further object of the present invention is to provide a therapy system for treating a subject located in the body of a patient with focused acoustic waves, having an ultrasound imaging system which supplies additional image information in comparison to the information available in conventional therapy systems for a better alignment of the therapy apparatus and the body of the patient.

The object pertaining to the ultrasound imaging apparatus is achieved in accordance with the principles of the present invention in an ultrasound imaging apparatus for imaging a subject which includes a source of acoustic waves which generates pulse-like acoustic waves converging in a focus, and an acoustic imaging means whose subject-side focal point lies in the region of the focus of the acoustic waves. The system further includes ultrasound sensor means, having an at least two-dimensional sensor matrix that is arranged in the region of the image-side focal point of the imaging means, for generating electrical output signals corresponding to the spatial distribution of the pressure of those parts of the pulse-like acoustic waves that have passed through the imaging means and been reflected at the subject to be imaged. The system includes image-generating electronics to which the output signals of the ultrasound sensor means are supplied and which generates a true-to-scale, real-time, three-dimensional image on the basis of the output signals. The image is displayed, preferably in perspective or two-dimensionally.

Whereas a multitude of pulse-like acoustic waves must be transmitted in the case of conventional ultrasound imaging apparatus functioning according to the tomogram principle in order to produce a single-tomogram (the resolution that can be achieved increases with the plurality of transmitted, pulse-like acoustic waves), the employment of an at least two-dimensional sensor matrix in accordance with the invention makes a single pulse-like acoustic wave adequate, independently of the resolution of the sensor matrix, to obtain the signals required for the imaging with respect to that surface wherein the pressure sensors of the sensor matrix are located. It is clear that a substantial gain in image-generating speed is thus achieved. In fact, a three-dimensional ultrasound image, given employment of a two-dimensional sensor matrix according to the invention and assuming identical acoustic running times can be produced in essentially the same time as a conventional two-dimensional ultrasound tomogram, so that three-dimensional ultrasound images can be produced in real-time. As used herein "ultrasound images produced in real-time" means ultrasound images that are produced in such a short time span that the condition represented in the image essentially coincides—even given moving subjects—with the current condition of the subject existing at the end of the imaging. The duration of the imaging procedure should not substantially exceed 200 to through 300 ms for medical purposes and should preferably be approximately 60 ms in terms of order of magnitude, since the presentation of the subject is then seen as flicker-free or and free of "jerking" motion given continuous, immediately succeeding imaging. The image generation can ensue in a way similar to conventional ultrasound apparatus (for example, time windowing). The image generation, however, can also ensue on the basis of a calculating procedure based on algorithms known from beam optics.

In an embodiment of the invention given the employment of a two-dimensional sensor matrix, the ultrasound sensor means is a planar sensor matrix divided into pressure sensors, which are preferably regularly arranged, and means for adjusting the distance between the sensor matrix and the imaging means. The adjustment ensues step-by-step, preferably with a step width that corresponds to the spacing between two pressure sensors of the two-dimensional sensor matrix that are immediately adjacent to one another. This achieves a measurement of the spatial distribution of the pressure which ensues at measuring points that are regularly arranged in spatial terms. If an acoustic lens is used as the acoustic imaging means, the adjustment of the distance between the sensor matrix and the imaging lens can ensue by adjusting the sensor matrix relative to the imaging lens as well as by adjusting the imaging lens relative to the sensor matrix. The adjustment preferably ensues in the direction of the acoustic axis of the imaging lens.

Whereas a plurality of pulse-like, acoustic waves, equal to the plurality of steps by which the distance between the sensor matrix and the imaging lens must be adjusted, are required when employing a two-dimensional sensor matrix for producing a three-dimensional image of the subject, a single, pulse-like acoustic wave suffices for producing the three-dimensional image of the subject in the case of a preferred embodiment of the invention. In this embodiment of the invention, the ultrasound sensor means is as a three-dimensional sensor matrix which contains pressure sensors in a preferably regular spatial arrangement. The acquisition of the spatial distribution of the pressure can thus ensue on the basis of the reflected parts of a single pulse-like acoustic wave. Thus the image repetition rate is ultimately upwardly limited only by the maximum repetition rate of the pulse-like acoustic waves in the case of a three-dimensional sensor matrix. The employment of a three-dimensional sensor matrix also offers the advantage that the image is free of all motion artifacts, which necessarily occur when more than one pulse-like acoustic wave is required for producing an image. The employment of a plurality of pulse-like acoustic waves could at most be necessary when the subject is of such a size that the produced image exceeds the dimensions of the three-dimensional sensor matrix, and thus a displacement of the sensor matrix and of the subject relative to one another is required in order to enable a complete imaging of the subject. Even in this case, however, only a few pulse-like acoustic waves suffice in order to produce the entire three-dimensional image.

In a further preferred embodiment, the three-dimensional sensor matrix can be realized in a technologically simple way in the form of a multilayer arrangement of polyvinylidene fluoride (PVDF) foils provided with electrodes, which are piezoelectrically activated and are subdivided into a plurality of pressure sensors. Such foils are commercially obtainable and can be easily provided with electrodes in a known way such that a two-dimensional sensor matrix is formed. A plurality of such two-dimensional sensor matrices are then connected, for example by gluing, to form a three-dimensional sensor matrix in the form of a multilayer arrangement.

In order to enable matching to different conditions, it can be expedient to dislocate the focus of the pulse-like, acoustic waves relative to the imaging lens. For this purpose, it is provided in a version of the invention that the imaging lens is as a lens having a variable focal length, the focal length given the displacement of the focus of the pulse-like acoustic waves being adjusted such that the focal point of the imaging lens at the subject side lies at least essentially in the focus of the pulse-like acoustic waves.

The imaging means need not be in the form of a physically present imaging lens, but can be formed by a simulation algorithm implemented in the image-producing electronics. An imaging lens having a variable focal length can also be simulated by such a simulation algorithm given the use of a physical imaging lens having a fixed focal length. Such algorithms are known from beam optics and are based on the fact that, given knowledge of the spatial pressure distribution and of the propagation mode of the reflected parts of the pulse-like acoustic waves, it is possible without further difficulty to calculate by applying the law of refraction that pressure distribution, which would arise if an imaging lens having defined acoustic properties were situated in the propagation path of the reflected parts.

In a further version of the invention, the source of acoustic waves generates shockwaves as the pulse-like acoustic waves. Shockwaves are acoustic pressure pulses having an extremely steep leading front.

The object of the invention pertaining to a therapy apparatus is inventively achieved in a therapy apparatus for treating a region located in the body of a patient with focused acoustic waves which contains a source of focused acoustic waves and contains an ultrasound imaging as described above as is locating system for locating a subject to the treated. The source of focused acoustic waves generates focused acoustic waves that serve the purpose of treatment as well as pulse-like acoustic waves that serve the purpose of imaging. A mark indicating the momentary position of the focus zone of the focused acoustic waves that serve the purpose of treatment is mixed into the image. Since the locating system of the therapy apparatus of the invention produces a three-dimensional image, additional information are available in order to align the thereby apparatus and the body of the patient to be treated relative to one another, such that an optimum position of the subject to be treated in the focus zone of the focused acoustic waves that serve the purpose of treatment is achieved. A more effective treatment which is gentler on the patient is thus possible. Particular advantages are achieved when the focus zone of the focused acoustic waves serving the purpose of treatment is small in comparison to the subject to be treated, and acoustic charging of tissue outside the subject to be treated must be avoided. By using the three-dimensional image information available in the case of the therapy apparatus of the invention, it is reliably and simply possible to relatively displace the focus zone of the focused acoustic waves that serve the purpose of treatment and the patient (or the subject) so that the focus zone exclusively "scans" the subject to be treated. A significant advantage is also that the locating means is capable of producing images in rapid succession, so that potential dislocations of the patient, or of the subject to be treated, relative to the therapy apparatus are immediately seen in the three-dimensional image information and can thus be taken into consideration in the therapy.

One version of the invention provides an acoustic lens that has a region for focusing the acoustic waves serving the purpose of treatment and a region that forms the imaging lens. In an economical and structurally simple way, a single component thus assumes the functions of the focusing device for the focused acoustic waves serving the purpose of treatment and assumes the function of the imaging lens.

In a preferred embodiment of the invention the imaging lens and the ultrasound sensor means form a unit that can be substituted for the ultrasound head, particularly the sector scanner, of a conventional ultrasound locating system. It is thus possible to work as needed in a conventional way using the conventional ultrasound locating system.

DESCRIPTION OF THE PREFERRED EMBODIMENTS

Figure 1:
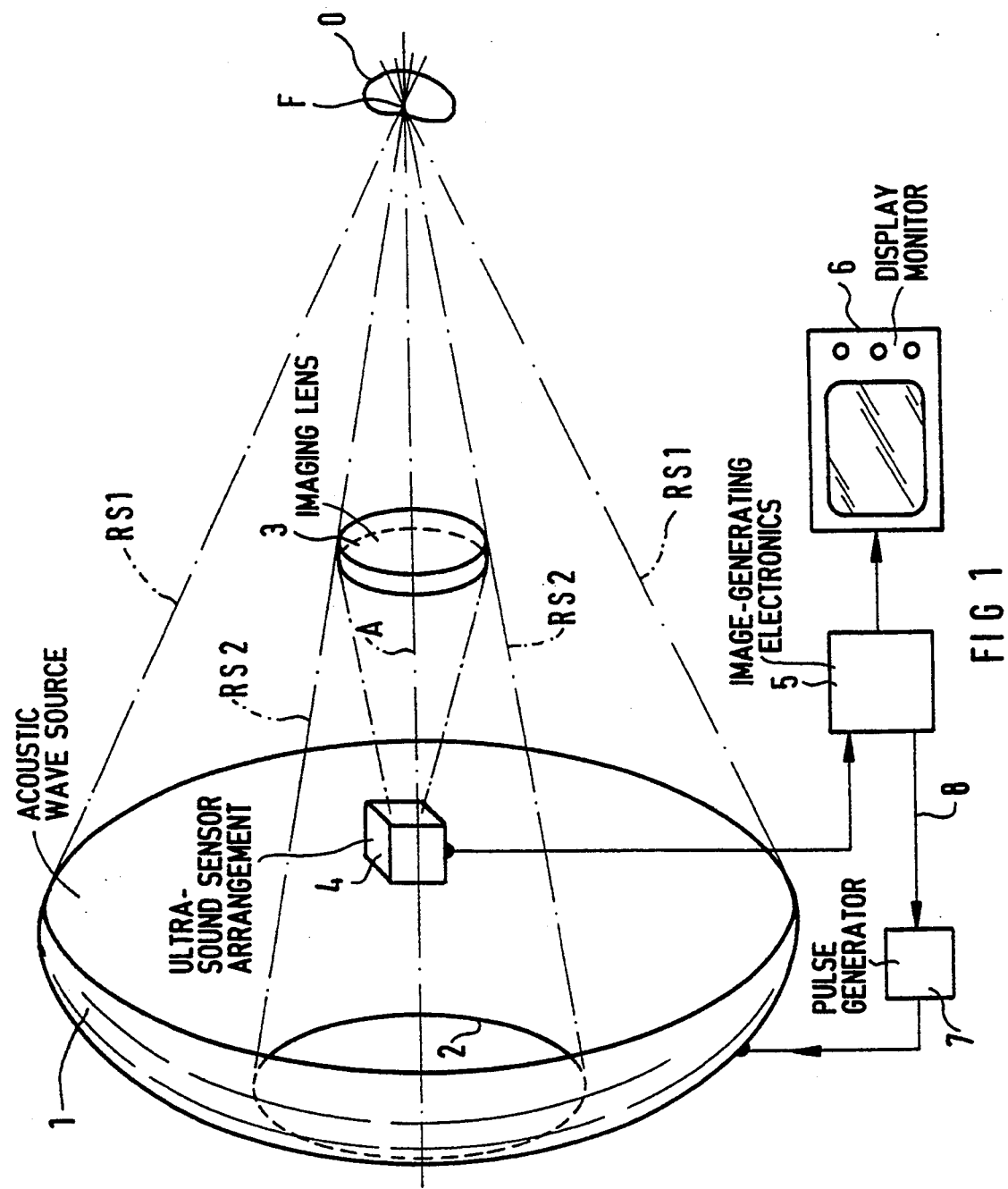
FIG. 1 is a perspective schematic illustration of an imaging system in accordance with the principles of the present invention.

The imaging apparatus of FIG. 1 has an acoustic wave source 1 in the form of a spherically curved, concave piezoelectric transducer which generates pulse-like acoustic waves converging in a focus F. The outermost rays of the source 1 are referenced RS1. The focus F is the center of curvature of the piezoelectric transducer. The focus F lies on the acoustic axis A of the arrangement, with respect to which the source 1 is substantially rotationally symmetric. The source 1 is fashioned such that a space that is substantially free of acoustic waves, and is approximately conical, surrounds the acoustic axis A, as indicted in FIG. 1 by the innermost rays RS2 of the acoustic waves emanating from the source 1. The space free of acoustic waves can be realized either by providing the source 1, as shown in FIG. 1, with a central opening 2, or by no emission of acoustic waves ensuing in the central region of the source 1.

An acoustic imaging means in the form of a lens 3, whose acoustic axis coincides with the acoustic axis A of the source 1 is arranged in the space free of acoustic waves. The focal point of the imaging lens 3 lies in the region of the focus F of the acoustic waves emanating from the source 1. An ultrasound sensor arrangement 4 is arranged in the region of the other focal point of the imaging lens 3. The ultrasound sensor arrangement 4 generates output signals corresponding to the spatial distribution of the pressure of the parts of the acoustic waves generated by the source 1 that are reflected at a subject O and have passed through the imaging lens 3.

Figure 2:
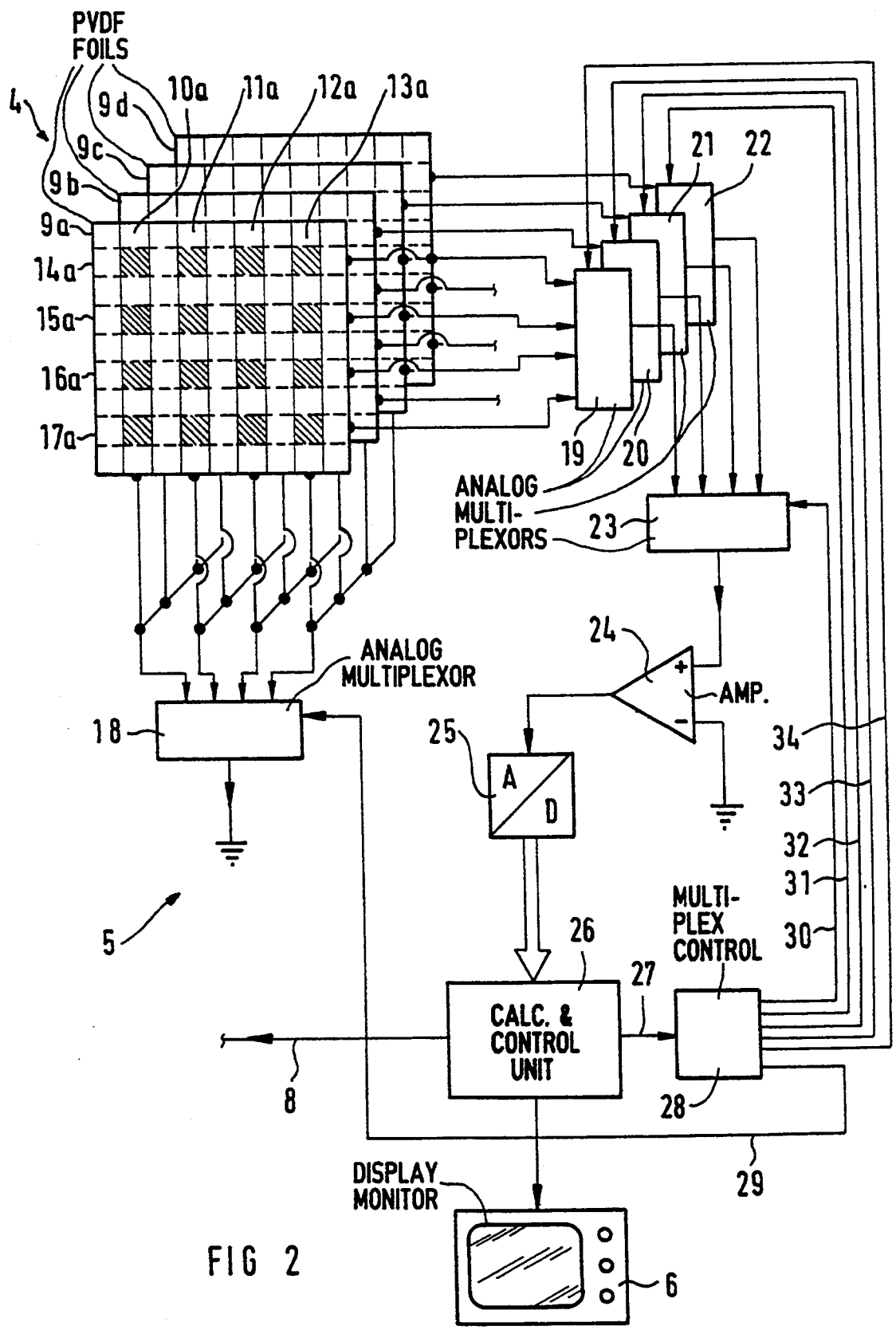
FIG. 2 is a schematic illustration of the ultrasound sensor arrangement of the imaging apparatus of FIG. 1 as well as the associated image-generating electronics in the form of a block circuit diagram.
Figure 3:
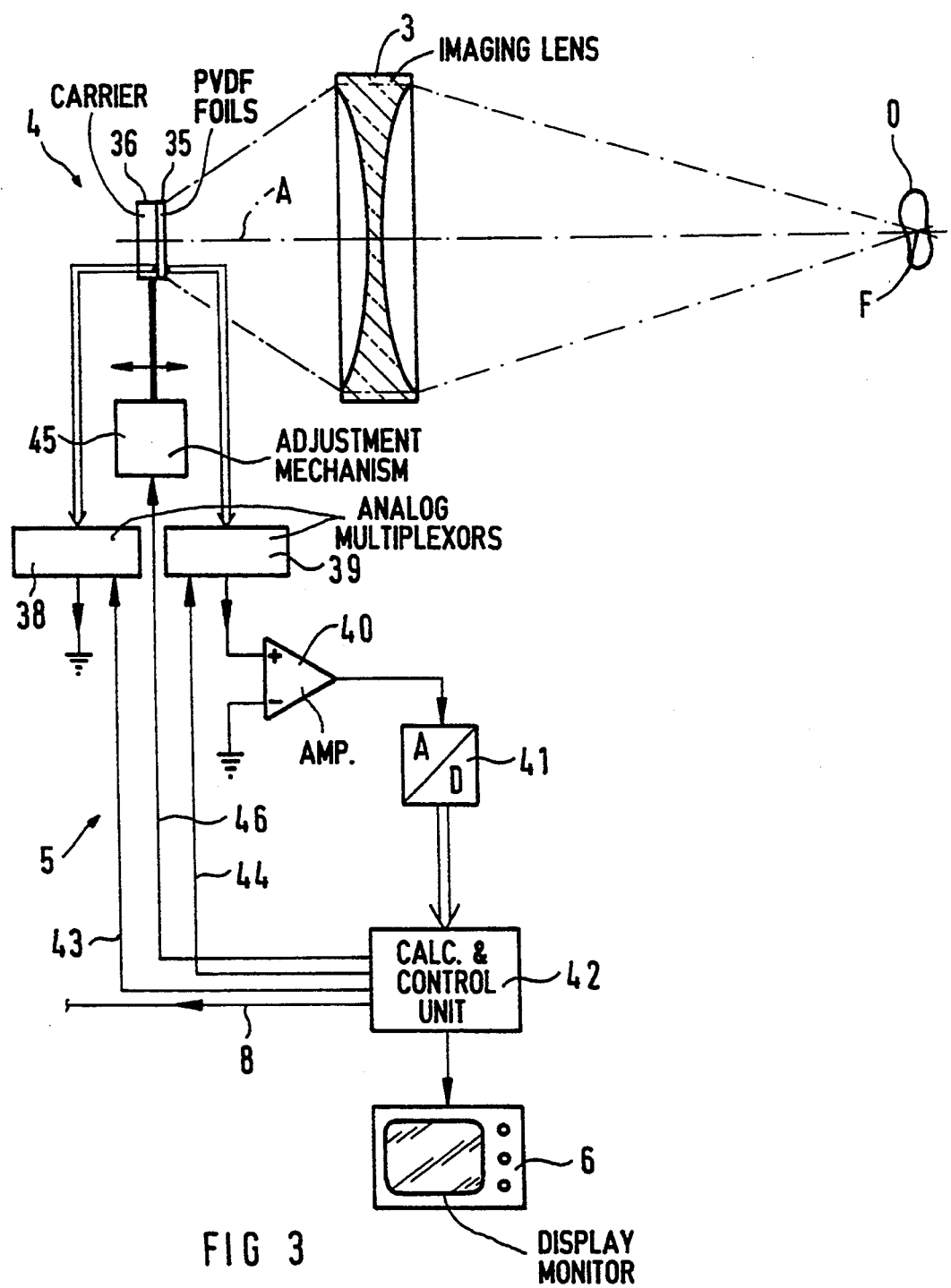
FIG. 3, in an illustration analogous to FIG. 2, shows a further version of an ultrasound sensor arrangement and associated image-generating electronics in accordance with the principles of the present invention.

The output signals of the ultrasound sensor arrangement 4, whose design shall be set forth in greater detail in conjunction with FIGS. 2 and 3, are supplied to image-generating electronics 5, which calculates a true-to-scale, real-time, three-dimensional image of the subject 8 on the basis of the output signals of the ultrasound sensor arrangement 4. This image of the subject 8 is displaced in perspective or two-dimensionally on a display monitor 6.

It is self-evident that acoustic coupling must be established between the subject O to be imaged and the source 1, as well as between the imaging lens 3 and the ultrasound sensor means 4. This can be produced, for example, by disposing the source 1, the imaging lens 3 and the ultrasound sensor arrangement 4, as well as the subject O to be imaged (which may be an object or a patient containing the subject O to be imaged) in a bath, (not shown in detail) that contains a liquid, for example water, as an acoustic propagation medium. It is also possible to contain the source 1, the imaging lens 3 and the ultrasound sensor means 4 in a housing (not shown) filled with a suitable acoustic propagation medium, the housing being closed in a known way with a preferably flexible application membrane that is provided for seating against the subject O to be imaged, or an object or patient that contains the subject O to be imaged.

An electric pulse generator 7 that charges the source 1 with electrical pulses is provided in order to drive the source 1 in the required way to generate an output of pulse-like acoustic waves. After being charged with such a pulse, the source 1 generates an acoustic pressure pulse that intensifies along its path through the acoustic propagation medium to form a shockwave. A shockwave is a pressure pulse having an extremely steep leading front. The pulse generator 7 is connected to the image-generating electronics 5 via a trigger line 8 and, given the arrival of a trigger pulse generated by the image-generating electronics 5, charges the source 1 with a high-voltage electrical pulse.

The structure of the ultrasound sensor arrangement 4 and the image-generating electronics 5 is shown in greater detail in FIG. 2. The ultrasound sensor arrangement 4 in this embodiment is a spatial 4×4×4 sensor matrix that is constructed of four piezoelectrically activated PVDF foils 9a through 9d. On its front side in the illustration, each of the PVDF foils 9a-9d is provided with four strip-shaped column electrodes that proceed at regular intervals from one another and parallel to one another. The column electrodes for the PVDF foil 9a are referenced 10a through 13a. Four strip-shaped row electrodes that respectively proceed at identical intervals from one another and parallel to one another are applied on the back sides of each of the PVDF foils 9a through 9d. The row electrodes of the PVDF foil 9a are indicated in broken lines and are referenced 14a through 17a. The row electrodes 14a through 17a proceed at an angle of 90° relative to the column electrodes 10a through 13a and thus overlap with the column electrodes 10a through 13a in the regions emphasized with hatching in FIG. 1. The PVDF foils 9b through 9d are each provided with column and row electrodes in a way analogous to the PVDF foil 9a. The row and column electrodes are preferably metallization strips applied on the respective PVDF foils. The regions emphasized with hatching in FIG. 2 act in a known way as piezoelectric pressure sensors, whereby the output signals of the individual pressure sensors can be tapped between that column electrode and that row electrode that overlap in the region of the respective pressure sensor.

The PVDF foils 9a through 9d are preferably connected to one another by gluing to form a multilayer arrangement with insulating layers (not shown in FIG. 2) therebetween that prevent shorts between electrodes of neighboring PVDF foils. The arrangement is made such that a spatially regular arrangement of the pressure sensors is formed, namely such that the centers of the pressure sensors lie in the intersections of the grid lines of a spatially cubic grating.

The column electrodes of the PVDF foils 9a through 9d can be connected to ground via a 4:1 analog multiplexer 18, such that, counting from the left, either all first, second, third or fourth column electrodes are at ground. In order to be able to read out the output signals of the pressure sensors, moreover, 4:1 analog multiplexers 19 through 22 are provided, their inputs being respectively connected to the row electrodes of one of the PVDF foils 9a through 9d. The outputs of the multiplexers 19 through 22 are connected to the inputs of a further 4:1 analog multiplexer 23 whose output is connected to the input of an amplifier 24. The output signal of the amplifier 24 is supplied to an analog-to-digital converter 25. The digital output data thereof are supplied to an electronic calculating and control unit 26 that is connected to the monitor 6. The calculating and control unit 26 also generates the trigger pulses for the pulse generator 7 that are supplied thereto via the trigger line 8. Moreover, the calculating and control unit 26 generates clock signals that are supplied via a control line 27 to a multiplexer controller 28 that controls the multiplexers 18 through 23 via control lines 29 through 34.

The drive of the multiplexers 18 through 23 ensues such that, following the generation of a shockwave with the source 1 and after expiration of a time span that approximately corresponds to the running time of the shockwave from the source 1 to focus F, the output signals of all pressure sensors are continuously interrogated in succession, are converted into digital data with the analog-to-digital converter 25 and are supplied to the calculating and control unit 26, wherein the data are intermediately stored. Based on the data received following the generation of a shockwave, the calculating and control unit 26 calculates a three-dimensional image of the subject to be imaged, for example on the basis of algorithms known from beam optics. This image is ultimately displayed on the monitor 6.

Since the output signals of the sensor matrix arising due to the reception of the parts of the shockwaves generated by the source 1 that are reflected at the subject to imaged are transient signals, it is necessary that the clock frequency with which the read-out of the output signals of the sensor matrix and of the analog-to-digital conversion ensues be correspondingly high, namely in the MHz range.

An increase in the processing speed is possible if the multiplexer 23 is omitted, and each of the multiplexers 19 through 22 is followed by an amplifier and by an analog-to-digital converter. A further increase in the processing speed is possible if each of the PVDF foils 9a through 9d has a plurality of analog-to-digital converters allocated to it, with one analog-to-digital converter being responsible for one group of pressure sensors (being responsible for only a single pressure sensor in the extreme case).

Instead of a three-dimensional sensor matrix as described in conjunction with FIG. 2, a two-dimensional sensor matrix can be employed according to FIG. 3. This contains a single PVDF foil 35 provided with electrodes in a way analogous to FIG. 2. The foil 35 is applied on a suitable carrier 36 as schematically shown in side view in FIG. 3. One of the column electrodes (which are not visible in FIG. 3) can be connected to ground via a 4:1 analog multiplexer 38. One of the row electrode (which are likewise not visible) can be connected via a 4:1 analog multiplexer 39 to an amplifier 40, whose output signals are supplied to an analog-to-digital converter 41. The digital output data thereof are again supplied to an electronic calculating and control unit 42, to which the monitor 6 is connected. The control and calculating unit 42 generates the trigger pulses for the pulse generator 7 that are supplied thereto via the control line 8. Moreover, the control and calculating unit generates the control pulses for the multiplexers 38 and 39 that are supplied thereto via control lines 43 and 44.

The read-out of the output signals of the pressure sensors of the PVDF foil 35 ensues in a way analogous to that set forth in conjunction with FIG. 2. In order to nonetheless be able to acquire the spatial distribution of the pressure of the parts of the shockwave reflected at a subject to be imaged, even though the PVDF foil 35 is only a two-dimensional sensor matrix, an adjustment mechanism 43 is provided which allows the PVDF foil 35 to be displaced relative to the imaging lens 3 in the direction of the acoustic axis A, as indicated by the double arrow x. When, as in the present case, the PVDF foil 35 represents a regular, two-dimensional 4×4 sensor matrix, it is expedient to adjust the PVDF foil 35 with the adjustment mechanism 43 so that it can assume four positions, which are selected such that a spatially regular arrangement of the centers of the pressure sensors arises. These pressure sensors again lie at the intersections of the grid lines of a spatial, cubic grating.

The adjustment mechanism 45 is actuated by the calculating and control unit 42 via a control line 46, such that the necessarily adjustment to the next position is completed before the output of a shockwave. The PVDF foil 35 upon the output of the first shockwave may be located, for example, in its position farthest from the imaging lens 3. Proceeding from that position, it will be adjusted into the position that is next closest to the imaging lens 3 before the output of the next shockwave, until it is ultimately brought into its position closest to the imaging lens 3 before the output of the fourth shockwave. The output signals for each of these positions are read out in a way analogous to FIG. 2, and are intermediately stored in the calculating and control unit 42 after analog-to-digital conversion. The unit 42 then calculates the three-dimensional image and causes it to be displayed on the monitor 6.

Figure 4:
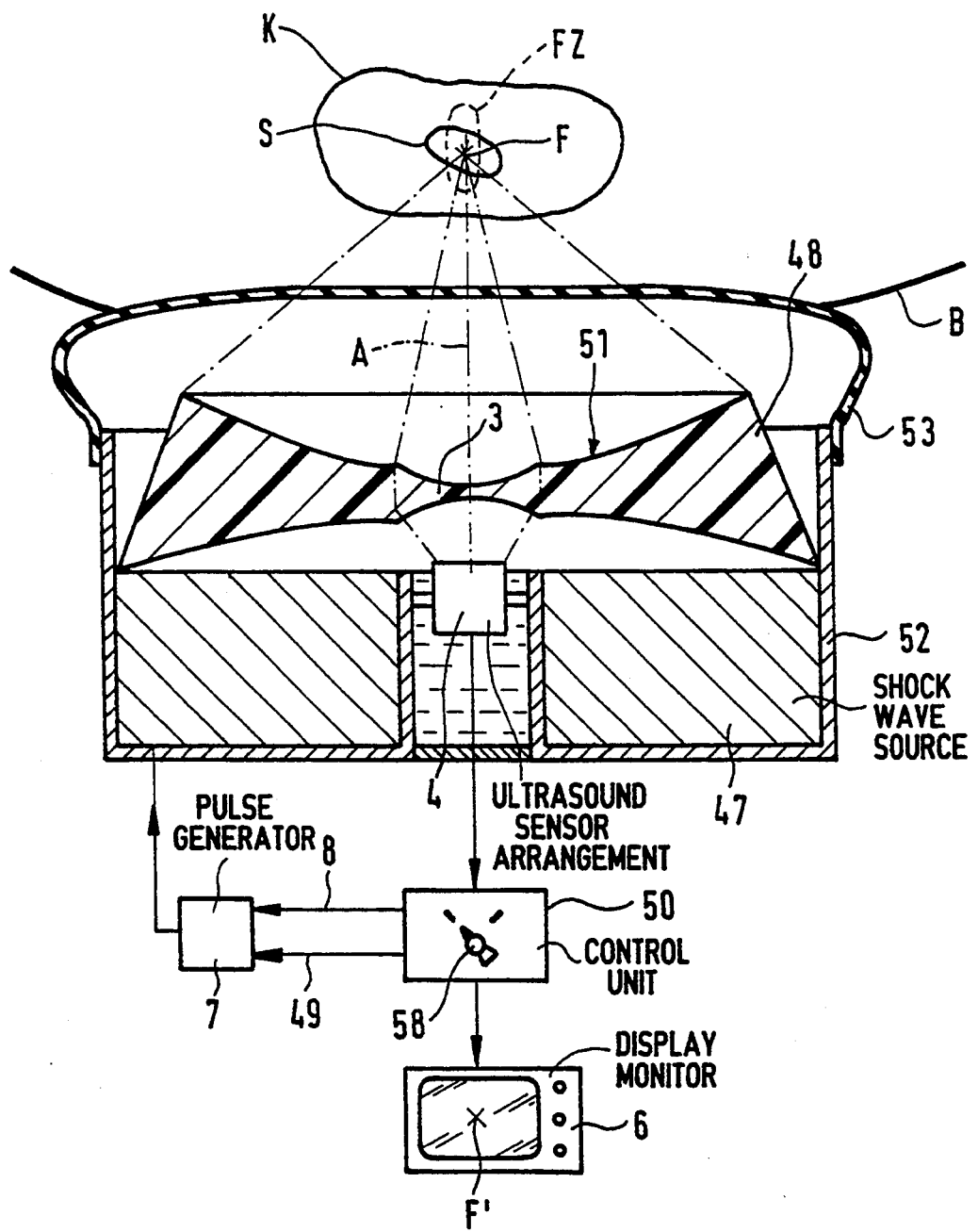
FIG. 4 is a schematic illustration of a therapy apparatus containing an imaging system of the invention as its locating system, shown in longitudinal section.

As is clear from the above, the ultrasound sensor arrangement 4 of FIG. 3—by contrast to that of FIG. 4—does not allow the three-dimensional image of the subject to be produced on the basis of the reflected portions of a single shockwave. On the contrary, a plurality of shockwaves is required, this plurality corresponding in number to the plurality of positions of the two-dimensional sensor matrix, i.e. of the PVDF foil 35. Consequently, an imaging system using the ultrasound sensor arrangement 4 of FIG. 3 must operate more slowly than an imaging system that contains the ultrasound sensor arrangement 4 of FIG. 2. As already set forth above, however, it is also assured in the case of the version according to FIG. 3 that the three-dimensional images can be produced in real-time and, thus, substantially faster than in the conventional systems.

FIG. 4 shows a therapy apparatus that contains an imaging system of the above-described type as its locating system. The therapy apparatus serves the purpose of treating a patient with focused acoustic waves, which are focused shockwaves in the case of the exemplary embodiment. For example, shockwaves are employed for non-invasive disintegration of calculi such as, for example, kidney stones. The therapy apparatus consequently contains a schematically-indicated shockwave source 47 that, for example, is an electromagnetic shockwave source of the species disclosed by European Application 0 188 750. The shockwave source 47 generates planar shockwaves that are focused with an acoustic positive lens 48 onto a focal zone referenced FZ. In order to be able to align the therapy apparatus and the body of a patient relative to one another such that a subject, for example, a kidney stone, to be charged with the generated shockwaves is located in the focal zone FZ of the shockwaves, the therapy apparatus contains an ultrasound locating system which, as already mentioned, is an imaging apparatus of the type set forth above. For generating the pulse-like acoustic waves required for imaging, however, no separate source for generating such waves is provided. On the contrary, the electrical pulse generator 7 is fashioned such that it charges the shockwave source 47 with high-intensity current pulses for generating shockwaves that serve therapeutic purposes and charges the shockwave source 47 with lower-intensity current pulses for generating shockwaves for the purpose of imaging. The corresponding switching ensues via a control line 49 connecting the pulse generator 7 to control electronics 50 that simultaneously contains the image-generating electronics.

The shockwave source 47 has an annular shape and consequently has a central opening in which the ultrasound sensor arrangement 4 is accepted, in a space free of shockwaves.

As a consequence of the space free of shockwaves, the possibility is present of fashioning the central region of the positive lens 48 as an imaging lens 3. The positive lens 48 and the imaging lens 3 thus form a single, shared lens body 51. The imaging lens 3 is shaped such that its focal point F at the subject side lies in the center of the focal zone FZ.

The control unit 50 includes a switch 58 with which the therapy apparatus can be optionally switched to a locating mode or a therapy mode. During the locating mode, the control unit 50 drives the pulse generator 7 such that it exclusively generates low-intensity shockwaves. The images produced with reference to the parts of the low-intensity shockwave reflected at the subject to be treated are displayed on the monitor 6, and the control unit 50 mixes a mark F' into the images which indicates the position of the center of the focal zone FZ. During the locating mode, the therapy means is aligned relative to the body B of a patient to be treated such that the image of the subject to be treated, for example the calculus S of a kidney K, coincides with the mark F'. In this case, the calculus S is located in the region of the focal zone FZ, as shown in FIG. 4.

When the desired alignment is assured, the switch 58 can be switched to the therapy mode. During the therapy mode, one or more high-intensity shockwaves are generated in alternation with one or more low-intensity shockwaves in order to achieve the desired therapeutic effect, for example the disintegration of the calculus S. An image of the region S to be treated is produced and displayed on the monitor 6 by emitting at least one low-intensity shockwave following every high-intensity shockwave, or following a pre-selectable plurality of high-intensity shockwaves. A continuous monitoring of the treatment is possible in this way. The shockwave source 47 the lens body 51 forming the positive lens 48 and the imaging lens 3 and the sensor means 4, moreover, are accepted in a housing that is filled with a suitable acoustic propagation medium, for example water, and is closed liquid-tight at its application end with a flexible coupling membrane 53. The coupling membrane 53 serves the purpose of pressing the therapy apparatus against the body B of the patient for acoustic coupling, as shown in FIG. 4.

Figure 5:
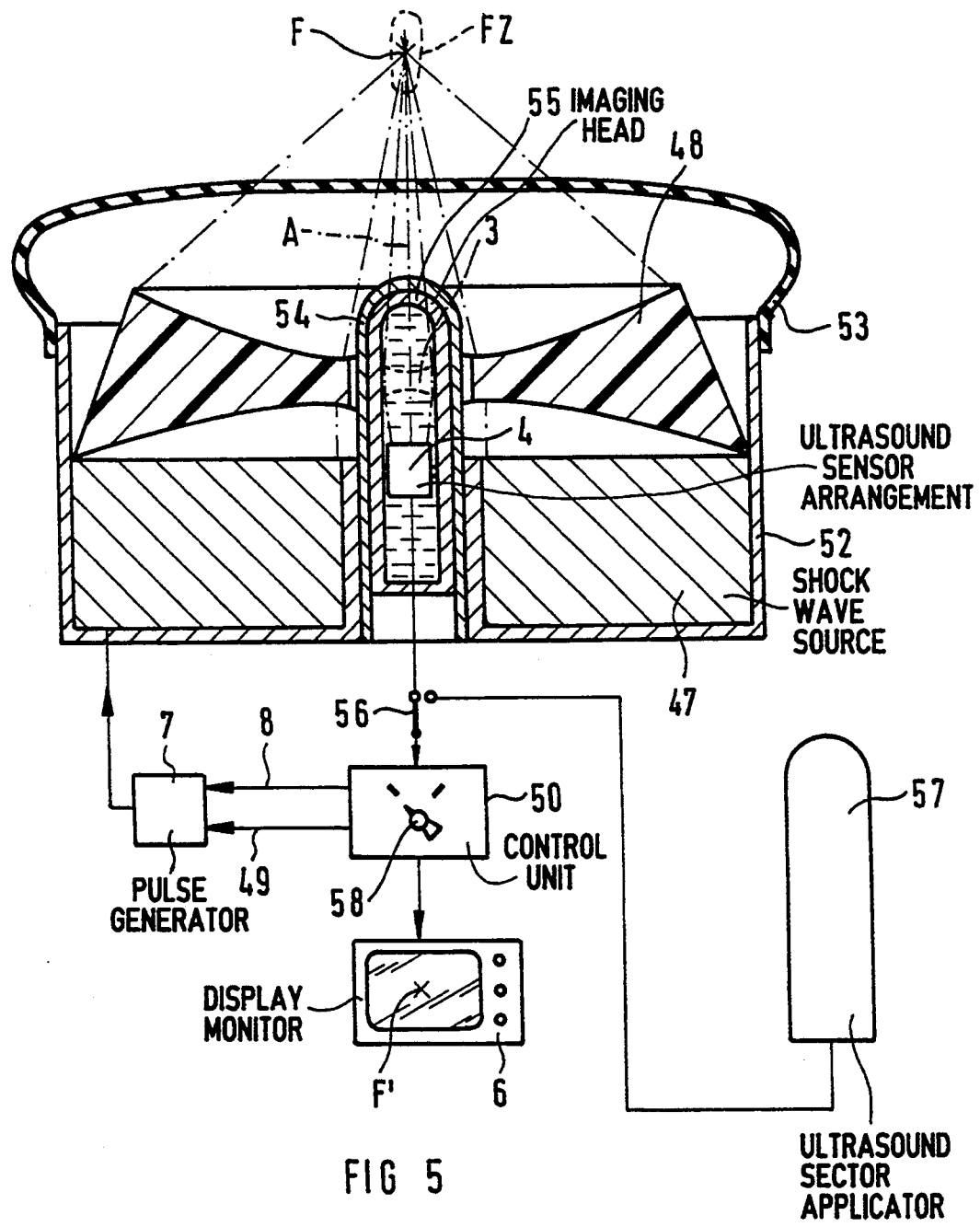
FIG. 5 shows a further version of the therapy system of FIG. 4.

The therapy apparatus shown in FIG. 5 differs from that set forth above in that the positive lens 48 also has a central opening aligned with the shockwave source 47. A tube 54, that is connected liquid-tight to the housing 52 extends through this central opening. An imaging head 55 filled with a satiable acoustic propagation medium and containing the imaging lens 3 as well as the ultrasound sensor arrangement 4 can be optionally introduced therein. When a switch 56 provided between the ultrasound sensor arrangement 4 and the control unit 50, is in the illustrated position and when the imaging head 55 is introduced into the tube 54, the therapy apparatus can be operated in the way set forth in conjunction with FIG. 4. When the switch 56 is brought into its other position and an ultrasound sector applicator 57 having the same dimensions is introduced into the tube 54 instead of the imaging head 55, conventional B-mode ultrasound images are produced instead of the three-dimensional ultrasound images, and are displayed on the monitor 6.

The imaging lens 3 is only shown with broken lines in the case of FIG. 5. This is intended to illustrate the possibility of omitting the imaging lens 3 and simulating it by an algorithm implemented in the image-generating electronics. This possibility exists not only in the case of the therapy apparatus of FIG. 5 but also given the embodiments of FIGS. 1 through 3 and 4.

The $4 \times 4 \times 4$ sensor matrix, or the $4 \times 4$ sensor matrix that can be brought in four positions, which have been set forth in conjunction with exemplary embodiments are only by way of example. Higher resolutions are possible without further difficulty, whereby the multiplexer arrangement required for the read-out of the output signals of the pressure sensors can be easily adapted to the necessary resolution.

In the exemplary embodiments that have been set forth, the three-dimensional image is calculated by the calculating and control unit 26. However, there is also the possibility—similar to conventional ultrasound equipment—of generating a three-dimensional image by time-windowing of the output signals of the sensor matrix.

The exemplary embodiments that relate to the therapy apparatus refer to the treatment of a patient with focused shockwaves. It is clear that therapy systems which emit different, focused acoustic waves for different treatment purposes, for example, ultrasound waves in the case of hyperthermia, can be similarly equipped in accordance with the principles of the present invention.

Although modifications and changes may be suggested by those skilled in the at, it is the intention of the inventors to embody within the patent warranted hereon all changes and modifications as reasonably and properly come within the scope of their contribution to the art.

We claim as our invention:

1. An ultrasound apparatus comprising:

means for generating a pulse-like acoustic wave converging a focus at a subject, resulting in an acoustic wave being reflected by said subject;

acoustic imaging means disposed for imaging said acoustic wave reflected from said subject, said acoustic imaging means having a focal point at a side thereof facing said subject disposed in the region of said focus of said acoustic wave, and said acoustic imaging means having a further focal point at a side thereof facing away from said focus of said acoustic wave;

ultrasound sensor means, having an at least two-dimensional sensor matrix formed by a plurality of pressure sensors disposed in at least one plane in the region of said further focal point of said acoustic imaging means, for generating electrical output signals corresponding to the spatial distribution, in a plane containing Said pressure sensors, of the pressure of said acoustic wave reflected by said subject and passing through said acoustic imaging means;

signal processing means, responsive to said electrical output signals, for generating a true-to-scale, real-time, three-dimensional image of said subject from said electrical output signals; and display means for displaying said image.

2. An ultrasound apparatus as claimed in claim 1 wherein said display means comprises means for displaying said image in perspective.

3. An ultrasound apparatus as claimed in claim 1 wherein said display means comprises means for two-dimensionally displaying said image.

4. An ultrasound apparatus as claimed in claim 1 further comprising means for adjusting a distance between said sensor matrix and said means for imaging.

5. An ultrasound apparatus as claimed in claim 4 wherein said ultrasound sensor means comprises a planar sensor matrix subdivided into a plurality of pressure sensors regularly disposed within said sensor matrix.

6. An ultrasound apparatus as claimed in claim 1 wherein said ultrasound sensor means comprises a three-dimensional sensor matrix containing a three-dimensional arrangement of a plurality of pressure sensors.

7. An ultrasound apparatus as claimed in claim 6 wherein said ultrasound sensor means comprises a three-dimensional sensor matrix containing a regular, three-dimensional arrangement of said plurality of pressure sensors.

8. An ultrasound apparatus as claimed in claim 6 wherein said three-dimensional sensor matrix comprises a plurality of layers of polyvinylidene fluoride foils, each foil subdivided into a plurality of piezoelectric pressure sensors, and each foil having a plurality of electrodes thereon forming electrodes for the respective piezoelectric pressure sensors.

9. An ultrasound apparatus as claimed in claim 1 wherein said means for generating said pulse-like acoustic waves comprises means for generating pulse-like acoustic waves converging at a focus which is displaceable relative to said means for imaging, and wherein said means for imaging comprises an acoustic lens having a variable focal length, and means for varying said focal length of said acoustic lens such that said focal point of said acoustic imaging means at said subject remains substantially coincident with said focus of said acoustic waves.

10. An ultrasound apparatus as claimed in claim 1 wherein said acoustic imaging means comprises electronic means for simulating an imaging lens by a simulation algorithm.

11. An ultrasound apparatus as claimed in claim 1 wherein said means for generating pulse-like acoustic waves comprises means for generating pulse-like shockwaves.

12. An ultrasound apparatus as claimed in claim 1 wherein said acoustic imaging means comprises an acoustic lens.

13. An ultrasound apparatus as claimed in claim 1 further comprising means for operating said means for generating said pulse-like acoustic waves to additionally generate acoustic therapy waves converging at a focal zone.

14. An ultrasound apparatus as claimed in claim 13 wherein said means far generating pulse-like acoustic waves comprises means for generating pulse-like shockwaves.

15. An ultrasound apparatus as claimed in claim 13 further comprising means for mixing a mark into said image on said means for displaying indicating a current position of said focal zone of said acoustic therapy waves.

16. An ultrasound apparatus as claimed in claim 13, wherein said acoustic therapy waves are pulse-like waves.

17. An ultrasound apparatus comprising:

a source of a pulse-like acoustic wave;

switchable means for selectively operating said source to generate a pulse-like acoustic imaging wave or acoustic therapy waves;

acoustic lens means, disposed between said source and a subject, for focusing said pulse-like acoustic imaging wave and said pulse-like acoustic therapy waves at a focus in said subject, resulting in an acoustic imaging wave being reflected by said subject, and for imaging said acoustic imaging wave reflected from said subject, said acoustic lens means having a focal point at a side thereof facing away from said subject;

ultrasound sensor means, having an at least two-dimensional sensor matrix formed by a plurality of pressure sensors disposed in at least one plane in the region of said focal point of said acoustic lens means, for generating electrical output signals corresponding to the spatial distribution, in a plane containing said sensors, of the pressure of said acoustic imaging wave reflected by said subject and passing through said acoustic lens means;

signal processing means, responsive to said electrical output signals, for generating a true-to-scale, real-time, three-dimensional image of said subject from said electrical output signals; and display means for displaying said image.

18. An ultrasound apparatus as claimed in claim 17 further comprising:

a housing containing said source of pulse-like acoustic waves and said acoustic lens means and having a cavity therein adapted to receive a standard ultrasound sector applicator, and wherein said ultrasound sensor means includes an ultrasound sensor means housing, in which said sensor matrix is disposed, having a shape conforming to said cavity.

19. An ultrasound apparatus as claimed in claim 17 wherein said display means comprises means for displaying said image in perspective.

20. An ultrasound apparatus as claimed in claim 17 wherein said display means comprises means for two-dimensionally displaying said image.

21. An ultrasound apparatus as claimed in claim 17 further comprising means for adjusting a distance between said sensor matrix and said means for imaging.

22. An ultrasound apparatus as claimed in claim 21 wherein said ultrasound sensor means comprises a planar sensor matrix subdivided into a plurality of pressure sensors regularly disposed within said sensor matrix.

23. An ultrasound apparatus as claimed in claim 17 wherein said ultrasound sensor means comprises a three-dimensional sensor matrix containing a three-dimensional arrangement of a plurality of pressure sensors.

24. An ultrasound apparatus as claimed in claim 23 wherein said ultrasound sensor means comprises a three-dimensional sensor matrix containing a regular, three-dimensional arrangement of said plurality of pressure sensors.

25. An ultrasound apparatus as claimed in claim 23 wherein said three-dimensional sensor matrix comprises a plurality of layers of polyvinylidene fluoride foils, each foil subdivided into a plurality of piezoelectric pressure sensors, and each foil having a plurality of electrodes thereon forming electrodes for the respective piezoelectric pressure sensors.

26. An ultrasound apparatus as claimed in claim 17 wherein said means for generating pulse-like acoustic waves comprises means for generating pulse-like shockwaves.

27. An ultrasound apparatus as claimed in claim 17 further comprising means for mixing a mark into said image on said means for displaying indicating a current position of said focal zone of said acoustic therapy waves.

28. An ultrasound apparatus as claimed in claim 17, wherein said lens means comprises a first region for focussing said acoustic therapy waves and a second region for focussing said acoustic imaging waves.

29. An ultrasound apparatus as claimed in claim 17, wherein said acoustic therapy waves are pulse-like waves.

30. An ultrasound apparatus comprising:
means for generating a pulse-like acoustic wave converging at a focus at a subject, resulting in an acoustic wave being reflected by said subject;
acoustic imaging means disposed for imaging said acoustic wave reflected from said subject, said acoustic imaging means having a focal point at a side thereof facing said subject disposed in the region of said focus of said acoustic wave, and said acoustic imaging means having a further focal point at a side thereof facing away from said focus of said acoustic wave;
ultrasound sensor means, having a two-dimensional planar sensor matrix formed by a plurality of pressure sensors disposed in the region of said further focal point of said acoustic imaging means, for generating electrical output signals corresponding to the spatial distribution of the pressure of said acoustic wave reflected by said subject and passing through said acoustic imaging means;
means for adjusting a distance between said sensor matrix and said means for imaging;
signal processing means, supplied with said electrical output signals, for generating a true-to-scale, real-time, three-dimensional image of said subject from said electrical output signals; and
display means for displaying said image.

31. An ultrasound apparatus as claimed in claim 30 wherein said ultrasound sensor means comprises a planar sensor matrix subdivided into a plurality of pressure sensors regularly disposed within said sensor matrix.

32. An ultrasound apparatus comprising:
means for generating a pulse-like acoustic wave converging at a displaceable focus at a subject, resulting in an acoustic wave being reflected by said subject;
acoustic lens disposed for imaging said acoustic wave reflected from said subject, said acoustic lens having a focal point at a side thereof facing said subject disposed in the region of said focus of said acoustic wave, and said acoustic lens having a further focal point at a side thereof facing away from said focus of said acoustic wave, said acoustic lens having a variable focal length;
means for varying said focal length of said acoustic lens such that said focal point of said acoustic lens at said subject remains substantially coincident with said focus of said acoustic waves;
ultrasound sensor means, having an at least two-dimensional sensor matrix disposed in the region of said further focal point of said acoustic lens, for generating electrical output signals corresponding to the spatial distribution of the pressure of said acoustic wave reflected by said subject and passing through said acoustic lens;
signal processing means, supplied with said electrical output signals, for generating a true-to-scale, real-time, three-dimensional image of said subject from said electrical output signals; and
display means for displaying said image.

33. An ultrasound apparatus comprising:
means for generating a pulse-like acoustic wave converging at a focus at a subject, resulting in an acoustic wave being reflected by said subject;
electronic means for simulating an imaging lens by a simulation algorithm for imaging said acoustic wave reflected from said subject, said simulated imaging lens having a focal point at a side thereof facing said subject in the region of said focus of said acoustic wave, and said simulated imaging lens having a further focal point at a side thereof facing away from said focus of said acoustic wave;
ultrasound sensor means, having an at least two-dimensional sensor matrix disposed in the region of said further focal point of said simulated imaging lens, for generating electrical output signals corresponding to the spatial distribution of the pressure of said acoustic wave reflected by said subject and passing through said acoustic imaging means;
signal processing means, supplied with said electrical output signals, for generating a true-to-scale, real-time, three-dimensional image of said subject from said electrical output signals; and
display means for displaying said image.

34. An ultrasound apparatus comprising:
means for generating a pulse-like acoustic wave converging at a focus at a subject, resulting in an acoustic wave being reflected by said subject;
acoustic imaging means disposed for imaging said acoustic wave reflected from said subject, said acoustic imaging means having a focal point at a side thereof facing said subject disposed in the region of said focus of said acoustic wave, and said acoustic imaging means having a further focal point at a side thereof facing away from said focus of said acoustic wave;
ultrasound sensor means, having an at least two-dimensional sensor matrix disposed in the region of said further focal point of said acoustic imaging means, for generating electrical output signals corresponding to the spatial distribution of the pressure of said acoustic wave reflected by said subject and passing through said acoustic imaging means;
signal processing means, supplied with said electrical output signals, for generating a true-to-scale, real-time, three-dimensional image of said subject from said electrical output signals;
display means for displaying said image; and
means for mixing a mark into said image on said means for displaying for indicating a current position of said focal zone of said acoustic therapy waves.

35. An ultrasound apparatus comprising:
a source of a pulse-like acoustic wave;

switchable means for selectively operating said source of pulse-like acoustic wave to generate a pulse-like acoustic imaging wave or a acoustic therapy wave;

acoustic lens means, disposed between said source of pulse-like acoustic wave and a subject, for focusing said pulse-like acoustic imaging wave and said pulse-like acoustic therapy,,wave at a focus in said subject, resulting in acoustic imaging wave being reflected by said subject, and for imaging said acoustic imaging wave reflected from said subject, said acoustic lens means having a focal point at a side thereof facing away from said subject;

ultrasound sensor means, having a two-dimensional planar sensor matrix formed by a plurality of pressure sensors disposed in the region of said focal point of said acoustic lens means, for generating electrical output signals corresponding to the spatial distribution of the pressure of said acoustic wave reflected by said subject and passing through said acoustic lens means;

means for adjusting a distance between said sensor matrix and said means for imaging;

signal processing means, supplied with said electrical output signals, for generating a true-to-scale, real-time, three-dimensional image of said subject from said electrical output signals; and display means for displaying said image.

36. An ultrasound apparatus as claimed in claim 35 wherein said ultrasound sensor means comprises a planar sensor matrix subdivided into a plurality of pressure sensors regularly disposed within said sensor matrix.

37. An ultrasound apparatus comprising:

a source of a pulse-like acoustic wave;

switchable means for selectively operating said source of pulse-like acoustic wave to generate a pulse-like acoustic imaging wave or acoustic therapy wave;

acoustic lens means, disposed between said source of pulse-like acoustic wave and a subject, for focusing said pulse-like acoustic imaging wave and said pulse-like acoustic therapy wave at a focus in said subject, resulting in acoustic imaging wave being reflected by said subject, and for imaging said acoustic imaging wave reflected from said subject, said acoustic lens means having a focal point at a side thereof facing away from said subject;

ultrasound sensor means, having an at least two-dimensional sensor matrix disposed in the region of said focal point of said acoustic lens means, for generating electrical output signals corresponding to the spatial distribution of the pressure of said acoustic wave reflected by said subject and passing through said acoustic lens means;

signal processing means, supplied with said electrical output signals, for generating a true-to-scale, real-time, three-dimensional image of said subject from said electrical output signals;

display means for displaying said image; and means for mixing a mark into said image on said means for displaying for indicating a current position of said focal zone of said acoustic therapy waves.

* * * * *